United States Patent [19]

Schell et al.

[11] Patent Number: 5,385,826
[45] Date of Patent: Jan. 31, 1995

[54] DIAGNOSTIC ASSAY FOR LYME DISEASE

[75] Inventors: Ronald F. Schell, Madison; Steven M. Callister, Onalaska, both of Wis.

[73] Assignee: Gundersen Medical Foundation, Ltd., Lacrosse, Wis.

[21] Appl. No.: 88,590

[22] Filed: Aug. 9, 1993

Related U.S. Application Data

[63] Continuation of Ser. No. 605,798, Oct. 31, 1990, abandoned, which is a continuation-in-part of Ser. No. 341,459, Apr. 21, 1989, abandoned.

[51] Int. Cl.$^6$ .................... C12Q 1/00; C12Q 1/02; G01N 33/53
[52] U.S. Cl. ................... 435/7.32; 435/7.2; 435/29; 435/34; 435/35; 436/804; 436/811; 436/821
[58] Field of Search ............... 435/7.2, 7.32, 29, 34, 435/35; 436/811, 804, 821

[56] References Cited

PUBLICATIONS

G. Zabucchi, G. D. Rottini, M. R. Soranzo, F. Tedesco and P. Patriarca, *A New Method for Assessment of Serum-Induced Damage to E. coli*, Journal of Immunological Methods, 57 (1983) pp. 253–264.
Steven M. Callister, William A. Agger, Ronald F. Schell, and Jay L. E. Ellingson, *Borrelia burgdorferi Infection Surrounding La Crosse, Wis.*, Journal of Clinical Microbiology, Dec. 1988, pp. 2632–2636.
Steven M. Callister, William A. Agger, Ronald F. Schell, and Karen M. Brand, *Efficacy of the Urinary Bladder for Isolation of Borrelia burgdorferi from Naturally Infected, Wild Peromyscus leucopus*, Journal of Clinical Microbiology, Apr. 1989, pp. 773–774.
Hedberg et al., 1987, J. Infect. Dis., 155, 1325.
Magnarelli, 1989, JAMA, 262, 3464.
Hedberg et al., 1990, Arch. Intern. Med., 150, 732.
Roantree et al., 1960, J. Clin. Invest. 39, 72.
Ross et al., 1985, J. Infect. Dis., 152, 1332.
Leptospirosis: Methods in Laboratory Diagnosis by C. R. Sulzer and W. L. Jones, 1980, U.S. Department of Health, Education and Welfare, Center for Disease Control, Atlanta, Ga.
Nelson et al., 1949, J. Exp. Med., 89, 369.
Warring G. W. 1964. Clinical use of treponemal tests in diagnosis of syphilis. Proceedings of World Forum on Syphilis and other Treponematoses, U.S. Department of Health, Education and Welfare, Washington, D.C.
Rein et al., 1980, Sex. Transmit. Dis., 7, 101.
Hardy, 1980, Sex. Transmit. Dis., 7, 145.
Pavia et al, Annals of the New York Academy of Sciences vol. 539 1988 pp. 410–413.
Kochi et al., Infection and Immunity, Feb. 1988, vol. 56 No. 2 pp. 314–321.
Nelson, et al. J. Exp. Med. vol. 89, pp. 369–393 (1949).
Schmitz et al., Infection and Immunity 56(9): 2336–2342 (1988).
Pennell et al., J. Clin. Microbiol. 25(11): 2218–2220 (1987).
Berardi et al., J. Infectious Diseases 158(4): 754–760 (1988).
Russell et al., J. Infectious Diseases 149(3): 465–470 (1984).

*Primary Examiner*—Michael G. Wityshyn
*Assistant Examiner*—Jane Williams
*Attorney, Agent, or Firm*—Allegretti & Witcoff, Ltd.

[57] ABSTRACT

A method of performing an assay to determine whether a patient has been exposed to or infected by *Borrelia burgdorferi* is disclosed which comprises collecting serum from the patient; preparing a sample mixture comprising a portion of the patient's serum and an inoculum of viable *Borrelia burgdorferi* organisms; incubating the sample mixture; determining the number of viable organisms remaining in the sample mixture after incubation; and comparing the number with the quantity of viable organisms remaining in a control. An assay kit is also disclosed which is useful for determining whether a patient has been exposed to or infected by *Borrelia burgdorferi*. The kit contains reagents necessary to practice the assay method disclosed herein. In its broadest form, the kit comprises an inoculum of viable *Borrelia burgdorferi* organisms. The kit can also contain an aliquot of normal serum, an aliquot of BSK medium and/or an aliquot of complement. Other reagents, tubes and other materials can also be included in the kits.

35 Claims, 16 Drawing Sheets

| NORMAL SERUM (INITIAL SURVEY) ||
|---|---|
| CASE-DEFINED SERUM # | % REDUCTION COMPARED TO NORMAL SERA CONTROL ($\bar{x}$) |
| 41 | 75 |
| 61 | 84 |
| 28 | 21 |
| 111 | 45 |
| 155 | 91 |
| 36 | 9 |
| 57 | 88 |
| 99 | 57 |
| 2 | 73 |
| 17 | 60 |
| 34 | 71 |
| 153 | 31 |
| 45 | 4 |
| 78 | 52 |
| 46 | 87 |
| 22 | 77 |
| 117 | 86 |
| 196 | 36 |
| 64 | 75 |
| 20 | 81 |
| 112 | 30 |

FIG. 1

| CASE-DEFINED SERUM # | % REDUCTION COMPARED TO NORMAL SERA CONTROL (n=3) |
|---|---|
| 41 | 57 |
| 61 | 58 |
| 28 | 0 |
| 111 | 0 |
| 155 | 84 |
| 36 | 30 |
| 57 | 78 |
| 99 | 7 |
| 2 | 61 |
| 17 | 28 |
| 34 | 52 |
| 153 | 21 |
| 45 | 19 |
| 78 | 47 |
| 46 | 76 |
| 22 | 67 |
| 117 | 87 |
| 196 | 64 |
| 64 | 74 |
| 20 | 60 |
| 112 | 30 |

| SERUM TREATMENT | SPLEEN | BLADDER |
|---|---|---|
| IMMUNE | 0/3 | 0/3 |
| NORMAL | 3/3 | 3/3 |

ᵃRESULTS ARE GIVEN AS NUMBER OF CULTURE POSITIVE TISSUES/TOTAL CULTURED.

DIAGNOSTIC ASSAY FOR LYME DISEASE

This application is a continuation of application Ser. No. 07/605,798, filed Oct. 31, 1990, now abandoned, which was a continuation-in-part of application Ser. No. 07/341,459, filed Apr. 21, 1989, now abandoned.

FIELD OF THE INVENTION

The present invention relates to clinical methods of detecting and evaluating infection of a patient with *Borrelia burgdorferi*, the organism responsible for Lyme disease. The method of the present invention can also be used to evaluate the immune status of a patient (e.g., to detect the presence of antibodies after immunization) and success of therapy (e.g., a decrease in antibody titer)

BACKGROUND OF THE INVENTION

Lyme disease, named after the site of an epidemic of oligoarticular arthritis [Steere et al., Arthritis Rheum. 20: 7-17 (1977)], is a multisystem infection often accompanied by an expanding skin lesion (erythema migrans) and concomitant or subsequent development or arthritic, cardiac, or neurologic complications [Reik et al., Medicine 58:281-294 (1979); Steere et al., Ann. Intern. Med 93 (1): 8-16 (1980); Steere et al., Ann. Intern. Med. 86:685-698 (1977); Steere et al., Ann. Intern. Med. 107: 725-731 (1987)]. Subsequent epidemiological studies have identified the deer tick, *Ixodes dammini*, as the primary vector of Lyme disease in North America [Burgdorfer et al., Science 216 1317-1319 (1982)] and a spirochete, *Borrelia burgdorferi* (hereinafter "*B. burgdorferi*"), as the causative agent of Lyme disease [Anderson et al., Am. J. Trop. Med. 32:818-824 (1983); Steere et al., N. Engl. J. Med. 308:733-740 (1983)]. Lyme disease is now the most common tick-borne illness recognized in the United States [Habicht et. al., Sci. Am. 257:78-83 (1987)].

Since Lyme disease may be more successfully treated if diagnosed early, an effective clinical assay for the detection of exposure to or infection with *B. burgdorferi* has been sought. Several prior assays, which rely on determination of the titer of antibodies to *B. burgdorferi* in patient sera, have used fluorescent-labelled anti-IgG antibodies [e.g., Magnarelli et. al., J. Clin. Microbiol. 20:181-184 (1984); Russell et al., J. Infect. Dis. 149:465-470 (1984); Steere et al., N. Engl. J. Med. 308: 733-740 (1983); Stiernstedt et al., J. Clin. Microbiol. 21: 819-825 (1985); Pennell et al., J. Clin. Microbiol. 25: 2218-2220 (1987)] and enzyme-labelled anti-IgG antibodies [e.g., Craft et al., J. Infect. Dis. 149: 789-795 (1984); Magnarelli et al., J. Clin. Microbiol. 20:181-184 (1984); Russell et al., J. Infect. Dis. 149: 465-470 (1984); Stiernstedt et al., J. Clin. Microbiol. 21: 819-825 (1985); Berardi et al., J. Infect. Dis. 158: 754-760 (1988)] to detect anti-*B. burgdorferi* antibodies which had previously been immobilized on a solid phase by binding to *B. burgdorferi* antigen. Unfortunately, these assays are of limited clinical use, since these antibody titers may not accurately indicate when the patient was exposed to *B. burgdorferi*. Furthermore, in many cases antibodies are not detected in patient sera by such assays until major symptoms of Lyme disease begin to appear making effective treatment more difficult if not impossible. In addition, these assays fail to define the immune status of the host or to predict the response of the host to infection or re-infection. It would, therefore, be desirable to provide an assay for exposure to or infection with *B. burgdorferi* which is capable of more accurate and more contemporaneous (i.e., closer to the date of exposure or infection) detection and which is capable of defining the immune status of a patient.

DESCRIPTION OF THE FIGURES

FIG. 1 is a table summarizing the reduction in the number of viable *B. burgdorferi* organisms in samples treated in Example 2 below.

FIG. 2 is a table summarizing the reduction in the number of viable *B. burgdorferi* organisms in samples treated in Example 3 below.

FIG. 4 is a graph relating to the effect of organism age on the method of the present invention.

SUMMARY OF THE INVENTION

Figure 3:
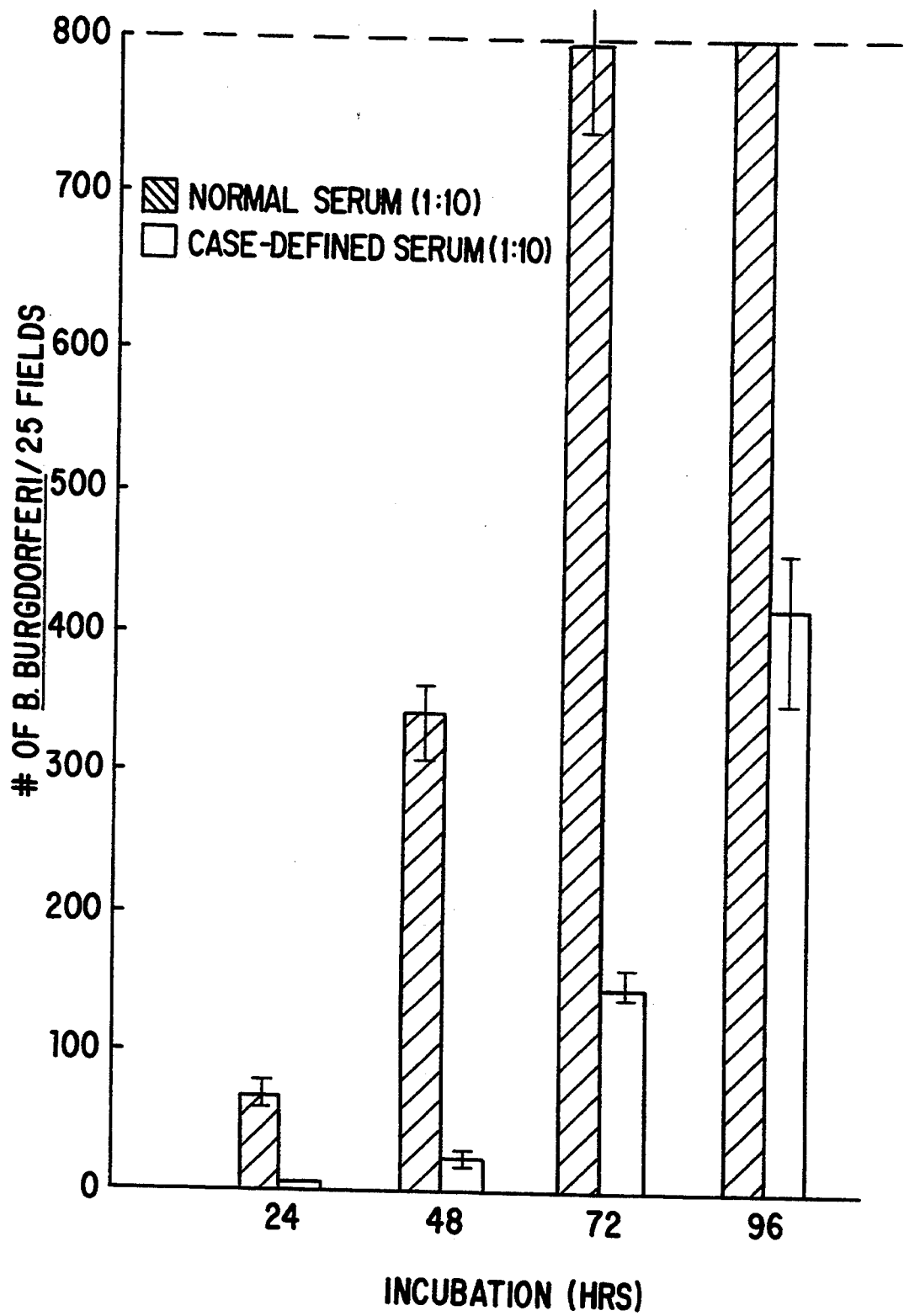
FIG. 3 is a graph relating to the continued growth (as described in Example 4) of samples after treatment in accordance with the methods of the present invention.

In accordance with the present invention, a method of performing an assay to determine whether a patient has been exposed to *Borrelia burgdorferi* (i.e., infected by, immunized or vaccinated with respect to or otherwise exposed to *Borrelia burgdorferi*) is disclosed which comprises collecting serum from the patient; preparing a sample mixture comprising a portion of the patient's serum and an inoculum of viable *Borrelia burgdorferi* organisms; incubating the sample mixture; determining the number of viable organisms remaining in the sample mixture after incubation; and comparing the number with the quantity of viable organisms remaining in a control. The patient can be either human or animal. The patient serum can be heat inactivated before conducting the assay such that immobilization or cell lysis is observed. In some instances, a source of complement can be added to the sample mixture. Serum also may be treated by ion exchange or other absorbing materials (e.g., cellulose phosphate) to remove anti-microbial agents if present.

By using the teachings of the present invention an assay can be performed "to determine whether a patient has been exposed to or infected by *B. burgdorferi*" regardless of the source of such exposure. For example, exposure can come in the form of infection by tick bite or by injection of *B. burgdorferi* or antigen in the form of a Lyme disease vaccine. In either event, the present invention can be employed to detect exposure or to determine the immune status of the patient.

Although *B. burgdorferi*, strain 297 is preferred for conducting the assay of the present invention, many strains can be used (e.g., strain B31). The methods of the present invention have been performed using numerous other strains including IS-17, Chicago, European and S-1-10 isolates. A strain which is common to the area in which the patient may have been exposed to *B. burgdorferi* may be preferred over other strains, if available. Preferably, the organisms used in the assay are "properly aged". "Properly aged" organisms are those that are at least about 72-74-hours old or in log phase growth, or those which have been subjected to a process which provides a similar effect in the sensitivity of the assay as aging (e.g., lyophilization of the organisms). A deposit of *B. burgdorferi*, strain 297 has been deposited with ATCC in accordance with the Budapest treaty on Apr. 21, 1989, as accession number 53899. *B. burgdorferi*, strain B31 is also available from ATCC as accession number 35210. Strains of *B. burgdorferi* can also be isolated according to the methods of Callister et al., J. Clin. Microbiol. 27: 773–774 (1989), which is incorporated herein in its entirety as if fully set forth. Although an inoculum of $10^4$–$10^5$ organisms is preferred for practicing the method of the present invention, other concentrations of organism can be used.

Incubation can be performed in any way known to the art which will promote growth of the organisms. Although longer or shorter incubation times can be used, preferably the samples are incubated at 32° C. for 30 minutes to 18 hours.

Preferably, the control is prepared by forming a control mixture of normal serum and an inoculum of viable *Borrelia burgdorferi* organisms and incubating the control mixture with the sample mixture.

Samples and controls are observed, preferably under a microscope, and the number of viable organisms are counted and compared to controls. Other means for counting viable organisms can also be used for practicing the present invention. For example, the organisms used to inoculate each sample could be labelled with a radioisotope, enzyme, fluorescent moiety, chemiluminescent moiety or other label such that the number or organisms can be determined by measuring the presence of the labeling material. Flow cytometry (employing known dyes such as propidium iodide) could be used to differentiate live and dead organisms. Samples could also be filtered after treatment and the remaining organisms on the filter could be determined. Catabolic or metabolic products or processes of the organisms could be measured to either determine the number of remaining organisms or the number of organisms which have been lysed and have released cell contents, or that differentiate viable and non-viable organisms. For example, the uptake of $^3$H-adenine could be monitored. Differences in the synthesis of DNA or RNA by patient and control samples could also be observed. Other means for quantitating the number of organisms remaining after treatment in accordance with the methods of the present invention or the number of organisms lysed, killed or immobilized by such treatment will be apparent to those skilled in the art and can be utilized in practicing the present invention.

"Viable organisms" are those organisms (a) which have not been lysed or have not disappeared, (b) which have not been immobilized or partially immobilized, and/or (c) which do not exhibit loss of refractivity. The number of viable organisms is counted because certain embodiments of the present invention may result in agglutination or complete lysis and disappearance of cells which, as a result, become unobservable.

As an article of manufacture, an assay kit is also disclosed which is useful for determining whether a patient has been exposed to or infected by *B. burgdorferi* (or to determine the immune status of a patient). The kit contains reagents necessary to practice the assay method disclosed herein. In its broadest form, the kit comprises an inoculum of viable *B. burgdorferi* organisms. The kit can also contain an aliquot of immune or normal serum and/or an aliquot of BSK medium. Other reagents, tubes, and other materials can also be included in the kits, such as complement or labelled or labelling moieties for use in detecting viable organisms (e.g., $^3$H-adenine or propidium iodide). The components of the kit can be viable and packaged by standard means applied in the diagnostic industry.

A method of conferring passive immunity upon a Lyme-susceptible (i.e., capable of being infected by *B. burgdorferi*) individual is also disclosed. The method comprises administering to the individual an amount of *Borrelia burgdorferi* positive (i.e., has been determined to have been taken from an individual who had been exposed to or infected with *B. burgdorferi*) serum sufficient to provide passive immunity. Preferably the serum is determined to be positive according to the assay methods of the present invention.

DETAILED DESCRIPTION OF THE INVENTION

Throughout the examples presented below, reference is made to Barbour-Stoenner-Kelly ("BSK") medium. BSK medium was prepared in accordance with Barbour, Yale J. Biol. Med 57:71–75 (1984), which is incorporated herein in its entirety by reference. After formulation, the BSK medium was subjected to a quality control scheme to ensure suitability for use. To check the quality of each batch of BSK medium, *B. burgdorferi* cultures were prepared which contained approximately $10^8$, $10^7$, $10^6$, $10^5$, $10^4$, $10^3$, $10^2$, 10 and 1 organism(s) in 6 ml BSk medium. The cultures were then incubated at 32° C. for 3 weeks. After incubation, the cultures were checked to see which culture tubes had shown growth. Preferably, the batch of BSK medium which grew morphologically normal *B. burgdorferi* from the lowest starting inoculum was used. Although BSK medium which does not meet this criterion can be used in practicing the present invention, it is preferred that the BSK medium pass these quality control measures. It is also preferred that the albumin used in formulating the BSK medium is fresh and of high quality (Callister et al., J. Clin. Microbiol. 28:363–365 (1990)).

EXAMPLE 1

Case defined patient sera to be evaluated for exposure to *B. burgdorferi* were collected. A normal serum pool was made from 10 sera from Wisconsin [which had been tested as negative by immunofluorescent assay (IFA)] patients which had no known exposure to *B. burgdorferi*. The patient serum and normal serum were diluted 1:5 with BSK medium. The diluted sera were then filter sterilized and heat inactivated at 56° C. for 45 minutes. Sera were freed of anti-microbiols by treatment with IONAC-C249 commercially available from Sybron Corp., New Jersey.

Individual samples were prepared by adding 100 ul of heat-inactivated patient serum or normal serum control to 100 ul of BSK medium containing approximately $10^5$ *B. burgdorferi* organisms. No source of complement was added. The samples were then incubated for 6 hours at 32° C. After incubation, the incubated samples were vortexed for one minute.

$3 \times 10$ ul of each sample and control were placed onto slides for counting. Viable organisms and organisms which were not immobilized were counted and the sample and control values were compared.

It was observed that serum from patient's who had been exposed to *B. burgdorferi* exhibited a significant decrease in the number of organisms which were viable and not immobilized as compared to the original inoculum. Some organisms were agglutinated or lysed and completely "disappeared." In contrast, the normal serum control showed no significant decrease. As a result, an observed decrease in the number of organisms from the number in the original inoculum is an indication of immune status or exposure to or infection with *B. burgdorferi*.

EXAMPLE 2

21 frozen samples of patient sera from 1985, which had previously been determined, by fluorescence immunoassay (IFA), as positive for *B. burgdorferi* infection were thawed and analyzed in accordance with the procedure described above in Example 1, except that the samples were incubated for 6 hours. Before analysis, all samples were filter sterilized (0.22 u filter) and/or treated to remove antibiotics. FIG. 1 summarizes the percent reduction in the number of *B. burgdorferi* organisms after treatment in accordance with the present invention. 19 (91%) of the samples tested positive to some degree (i.e., showed a reduction in organism number) in the assay of the present invention. No normal serum controls showed any significant decrease in organism number. The assay of the present invention detected that 90% of the previous case defined samples were, in fact, positive for *B. burgdorferi* exposure or infection.

EXAMPLE 3

The same 21 samples were again tested as described in Example 2, with the exception that organisms aged for 72 hours were added to each sample and the samples were incubated for 18 hours. FIG. 2 summarizes the results of these tests. Again, 19 of 21 samples tested positive in the assay of the present invention. However, the use of aged organisms and a longer incubation time decreased the overall variability of the assay.

EXAMPLE 4

To confirm that the number of remaining viable *B. burgdorferi* was actually decreased by the method of the present invention, 6 ml of fresh BSK medium was added to one patient sample (number 57 in FIGS. 1 and 2) and a normal serum sample from Example 2. The samples were then reincubated at 32° C. The number of organisms in each sample was counted 24, 48, 72, and 96 hours after addition of the fresh BSK medium. The count results are summarized in FIG. 3. At each time interval, the normal serum control was observed to contain significantly more organisms than the patient sample, thus confirming that the number of viable organisms in the patient sample had been significantly reduced.

EXAMPLE 5

Figure 4:
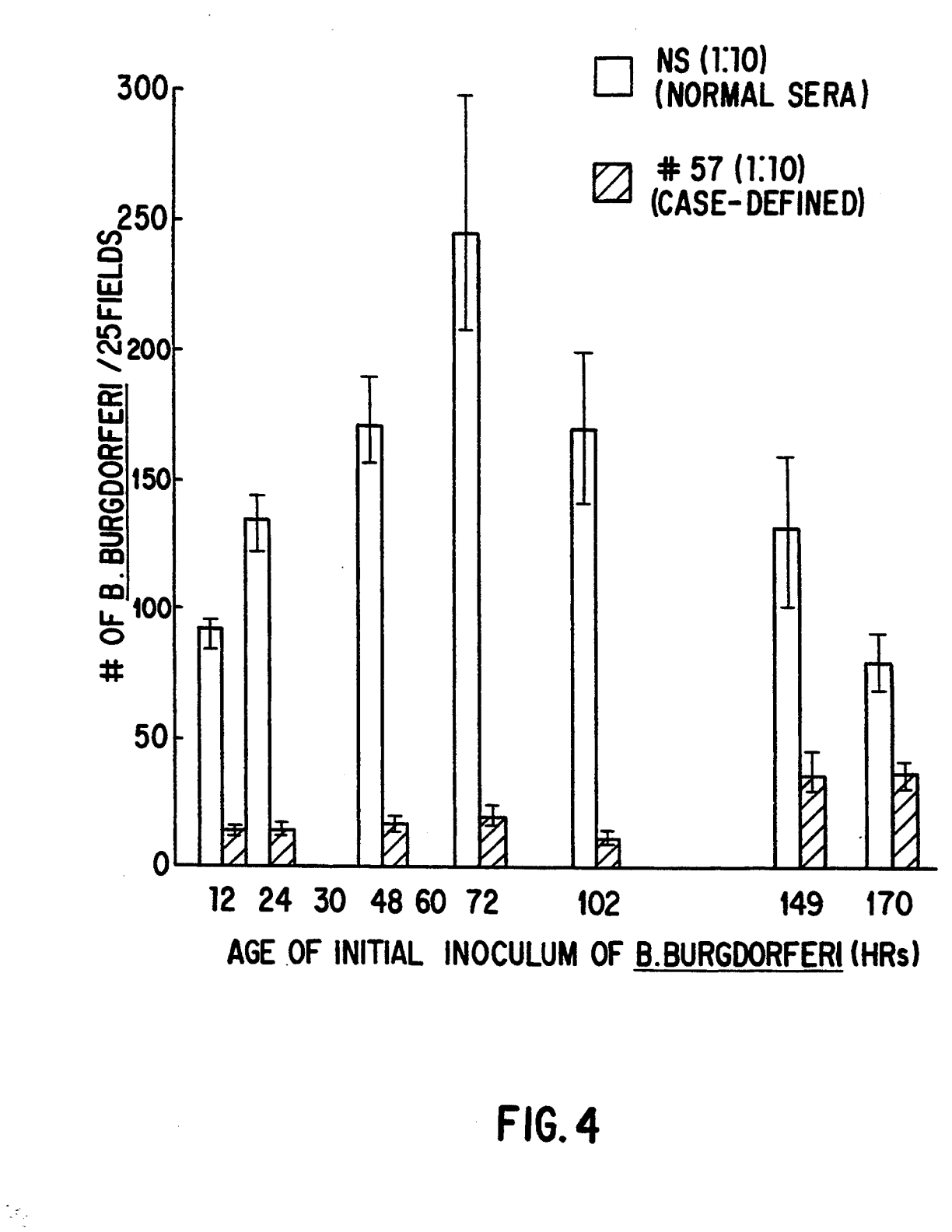

The effect of the age of *B. burgdorferi* organisms employed in the method of the present invention was examined. Samples were prepared as described above in Example 2, except that organisms were aged for 12, 24, 51, 74, 102, 149 and 170 hours before inoculating separate samples. Test results are summarized in FIG. 4. All samples exhibited a significant reduction in the number of viable organisms, although 74-hours organisms appeared to maximize the reduction observed. The results demonstrate that properly aged organisms, or organisms subjected to processes that achieve the same effect (e.g., lyophilization), change the sensitivity of the assay.

EXAMPLE 6

Figure 5:
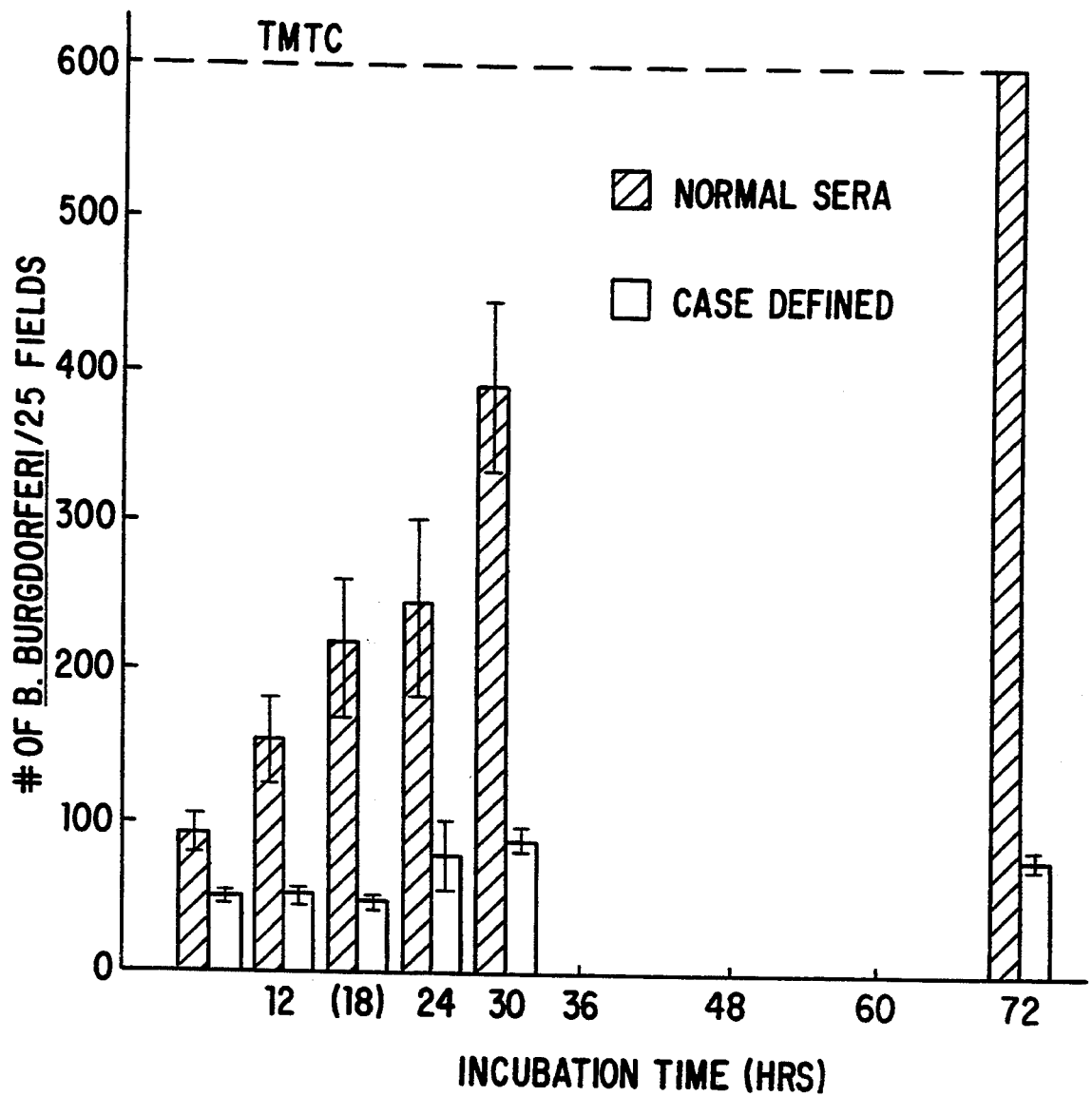
FIG. 5 is a graph relating to the effect of incubation time on the method of the present invention.

The effect of different incubation times was examined. Samples were prepared as described above in Example 2, except that the assay was performed (counted) after 6, 12, 18, 24, 30 and 72 hour incubation intervals. Test results are summarized in FIG. 5. All samples exhibited a significant reduction in the number of viable organisms and the magnitude of the reduction (i.e., sensitivity) increased with longer incubation. Although greater reduction is observed with longer incubation times, time constraints may make longer incubation time impractical. Preferably the incubation time is 30 minutes to 18 hours.

EXAMPLE 7

Figure 6:
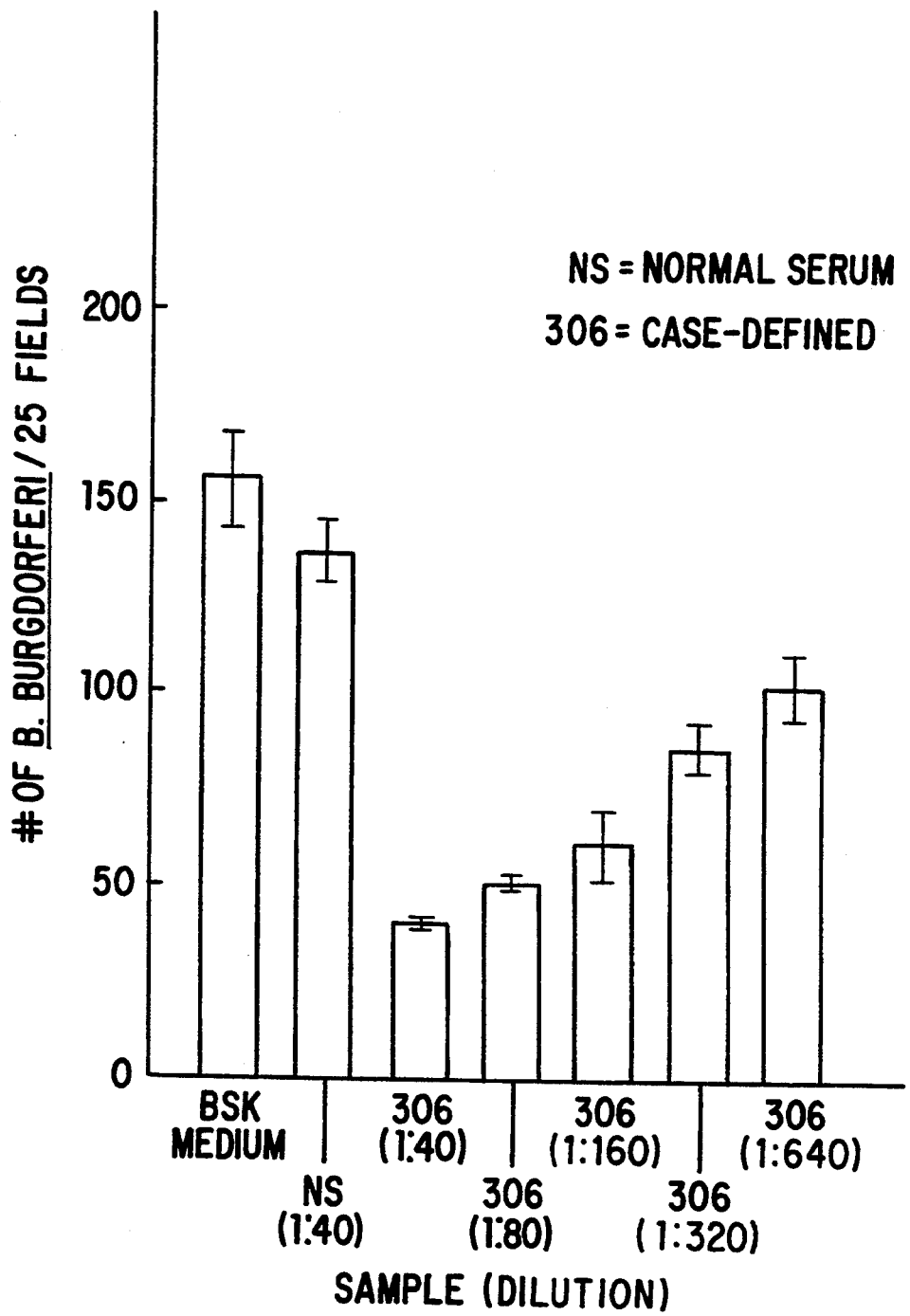
FIG. 6 is a graph relating to the effect of patient serum dilution on the method of the present invention.

The effect of diluting the patient serum was examined. Samples were prepared as described in Examples 2, except that dilutions of patient sera of 1:40, 1:80, 1:160, 1:320 and 1:640 were prepared. Test results are summarized in FIG. 6. Dilution of patient sera significantly decreased the immobilization, agglutination or lytic effect of the method of the present invention.

EXAMPLE 8

Figure 7:
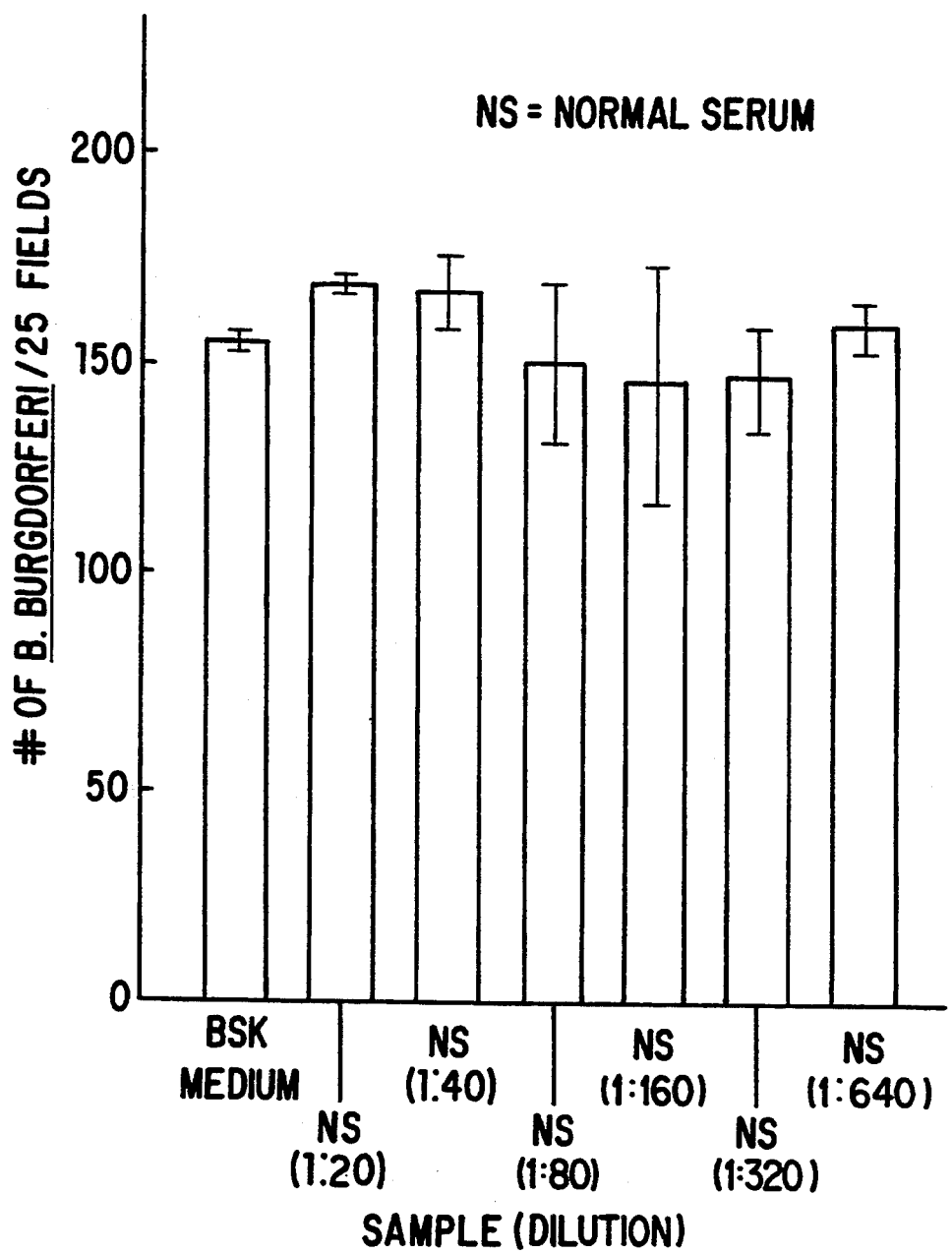
FIG. 7 is a graph comparing the immobilizing/lytic activity of normal serum and BSK medium.

The immobilization, agglutination or lytic effect of a pooled normal serum as compared to BSK medium was examined. Samples of BSK medium and normal serum were prepared as described in Example 2. Samples were prepared for 1:20, 1:40, 1:50, 1:60, 1:70 and 1:80 dilutions of normal serum. Test results are summarized in FIG. 7. Normal serum samples exhibited no significant effect in comparison with BSK medium.

In addition, five pools (each containing 6 normal sera) were also examined. These pools of normal sera failed to reduce the number of organisms in the assay of the present invention when compared with BSK medium containing organisms.

EXAMPLE 9

Normal and *B. burgdorferi*-infected sera were obtained from male LSH/SsLak hamsters (animals from Charles River Breeding Laboratories, Wilmington, Mass.). The animals were housed four per cage at ambient temperature. Normal serum was obtained from 6–8 week old hamsters.

*B. burgdorferi* sensitized (infected) serum was obtained from hamsters that had been injected with 0.2–0.4 ml of $5 \times 10^6$ cells/ml suspension of *B. burgdorferi* (strain 297). Injections were subcutaneous in the hind paws of the hamsters. Blood was drawn from infected hamsters by cardiac puncture at 3, 5 and 7 weeks after injection. Serum was obtained from the collected blood by standard techniques. The sera were filter sterilized, diluted 1:5 with BSK medium and tested in the assay of the present invention. Prior to use in the assays described below, the sera were heat inactivated for 45 minutes at 56° C.

Sample mixtures were prepared with normal human serum, normal hamster serum and with 3, 5, and 7 week post-infection serum as described in Example 3. The samples were then incubated for 18 hours at 32° C.

Triplicate samples of 10 ul were removed from each incubated sample mixture and control mixture and counted as previously described. The sensitized serum samples exhibited significant decreases in the number of viable organisms in comparison to both the human and hamster normal serum controls. No significant difference was observed between the human and hamster normal serum controls.

Fresh BSK was added to samples which were then reincubated and counted as described in Example 4. Again, the counts confirmed that the number of viable organisms had actually been reduced.

EXAMPLE 10

Sensitized serum samples from dogs have also been observed to significantly reduce the number of viable organisms remaining after treatment in accordance with the methods of the present invention. Normal serum from dogs did not reduce the number or organisms observed. Activity was also found in other animals (i.e., horses) suspected of having Lyme disease.

EXAMPLE 11

Figure 8:
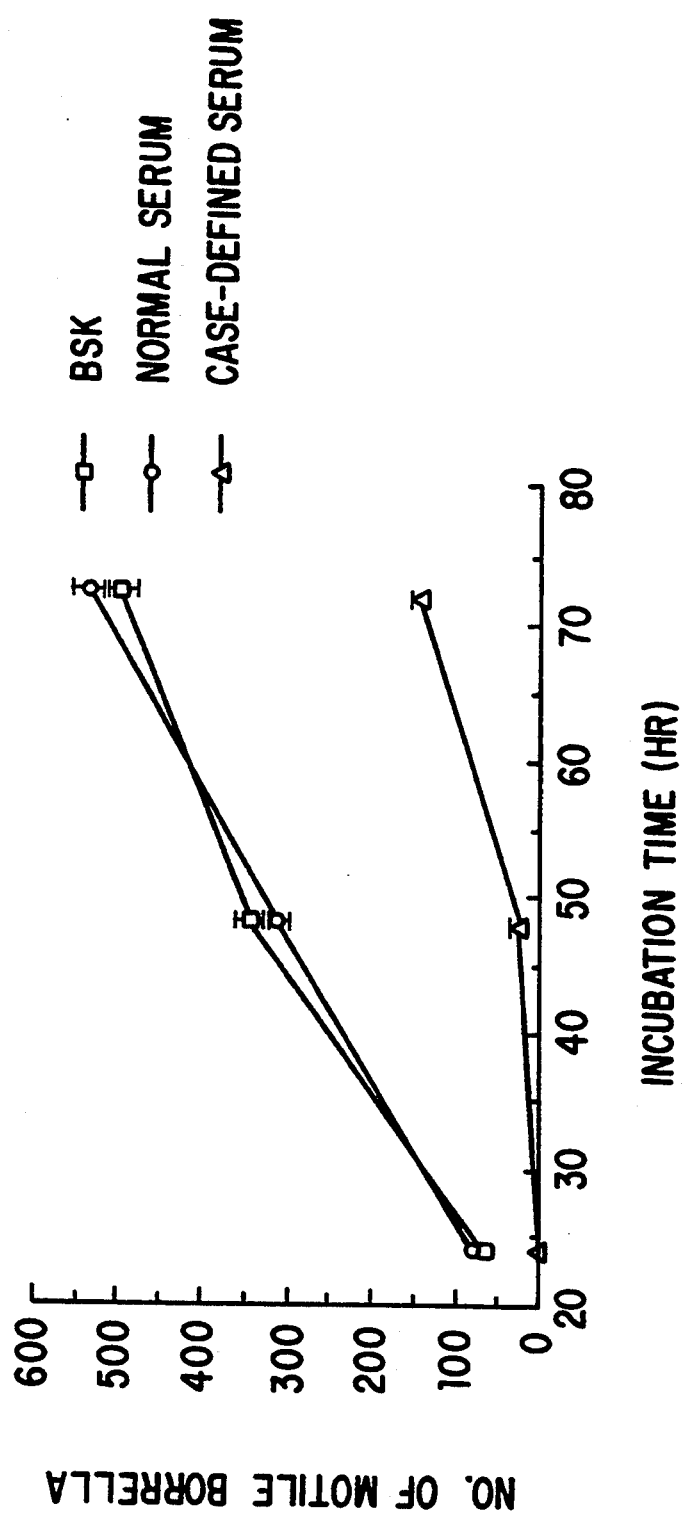
FIGS. 8-17 are graphs and tables summarizing data collected in Examples 11-21.

A normal serum and a Lyme disease serum were assayed as described in Example 1. After 18 hours of incubation, the Lyme disease serum caused a 97% reduction in motile B. burgdoferi compared to normal serum and BSK (not shown). Fresh BSK was added to samples which were then reincubated and counted as described in Example 4. After 24, 48, and 72 hours, the counts confirmed that the numbers of viable organisms had been reduced (FIG. 8).

EXAMPLE 12

A radiolabel assay which utilizes the incorporation of $^3$H-adenine into viable B. burgdorferi was developed to determine the number of viable B. burgdorferi in sample and control mixtures. This increased the overall sensitivity of the assay by enabling fewer organisms to be used and decreasing the standard error between duplicate or triplicate samples. The assay was performed essentially as stated in Example 1. However, after the initial incubation, 2 ul of $^3$H-adenine and 798 ul of fresh BSK was added to the assay tubes. All assays were subsequently incubated for 4–6 additional days at 32° C. and the counts per minute of incorporated $^3$H-adenine was determined using scintillation counting.

EXAMPLE 13

Figure 9:
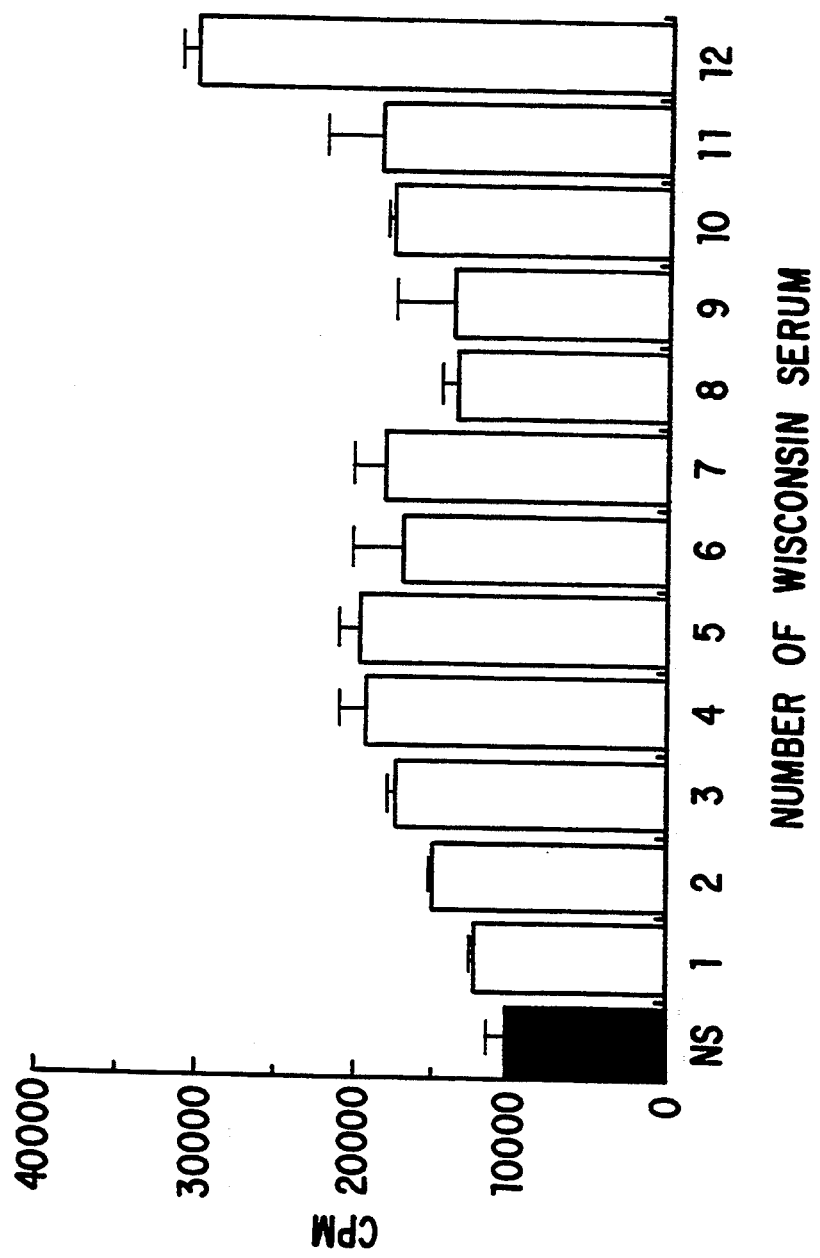
Figure 10:
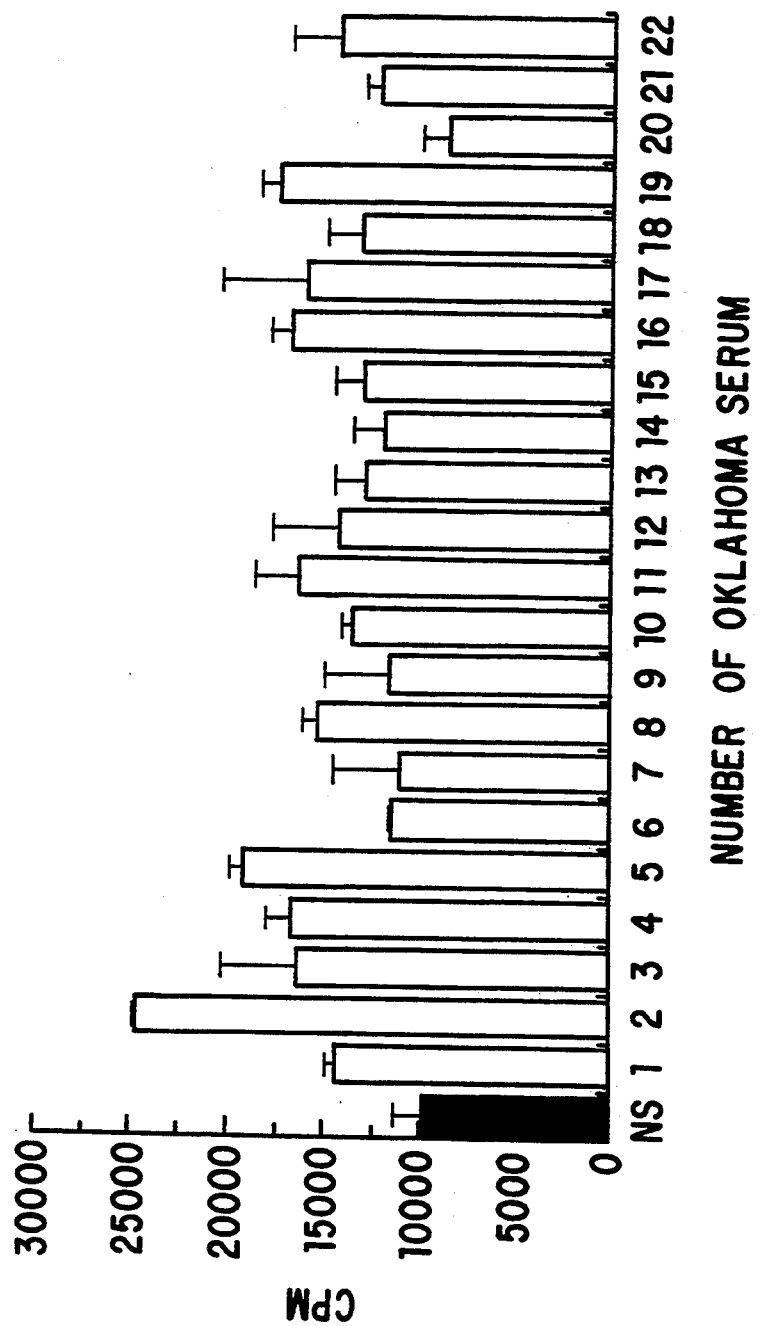

12 individual normal sera from Wisconsin and 22 individual normal sera from Oklahoma, which had previously been determined by case review and IFA to be negative for B. burgdorferi infection were analyzed in accordance with the procedure described in Example 12. FIGS. 9 and 10 summarizes the borreliacidal activity. None of the tested normal serum caused B. burgdorferi killing compared to pooled normal sera.

EXAMPLE 14

Figure 11:
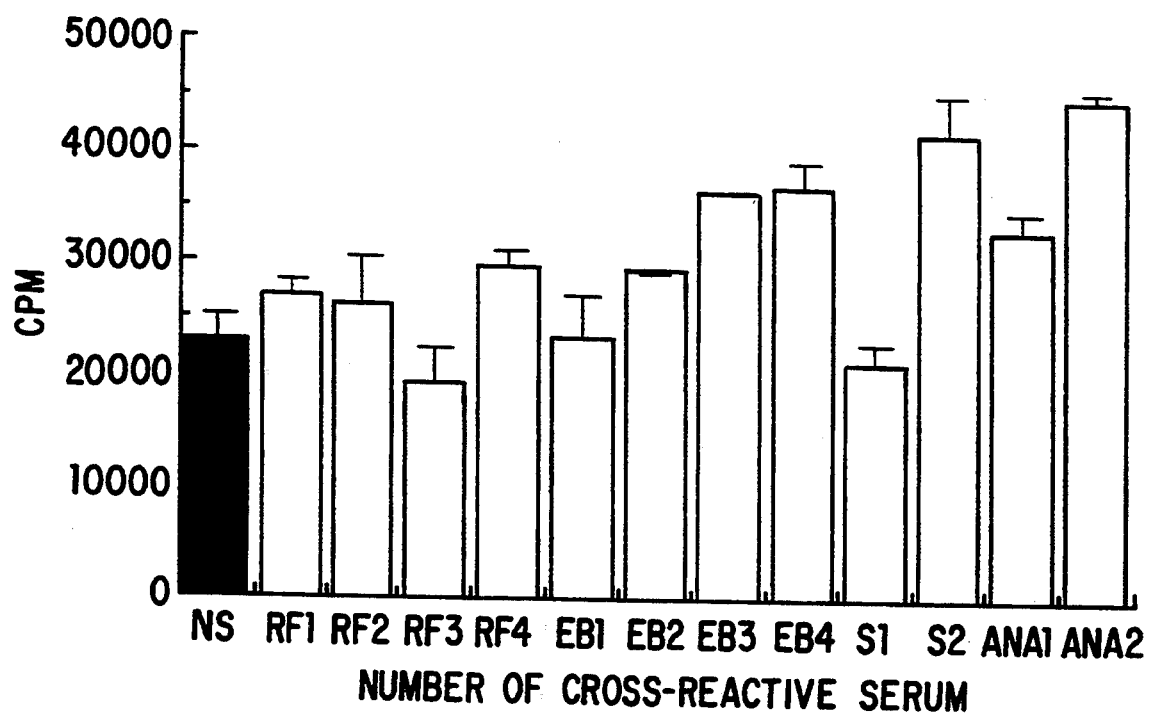

4 individual sera from patients with rheumatoid factor, 4 patients with mononucleosis, 2 patients with syphilis, and 2 patients with anti-nuclear antibody were analyzed in accordance with the procedure described in Example 12. FIG. 11 summarizes the borreliacidal activity. None of the potentially cross-reactive sera caused reductions of B. burgdorferi compared to pooled normal serum.

EXAMPLE 15

Figure 12:
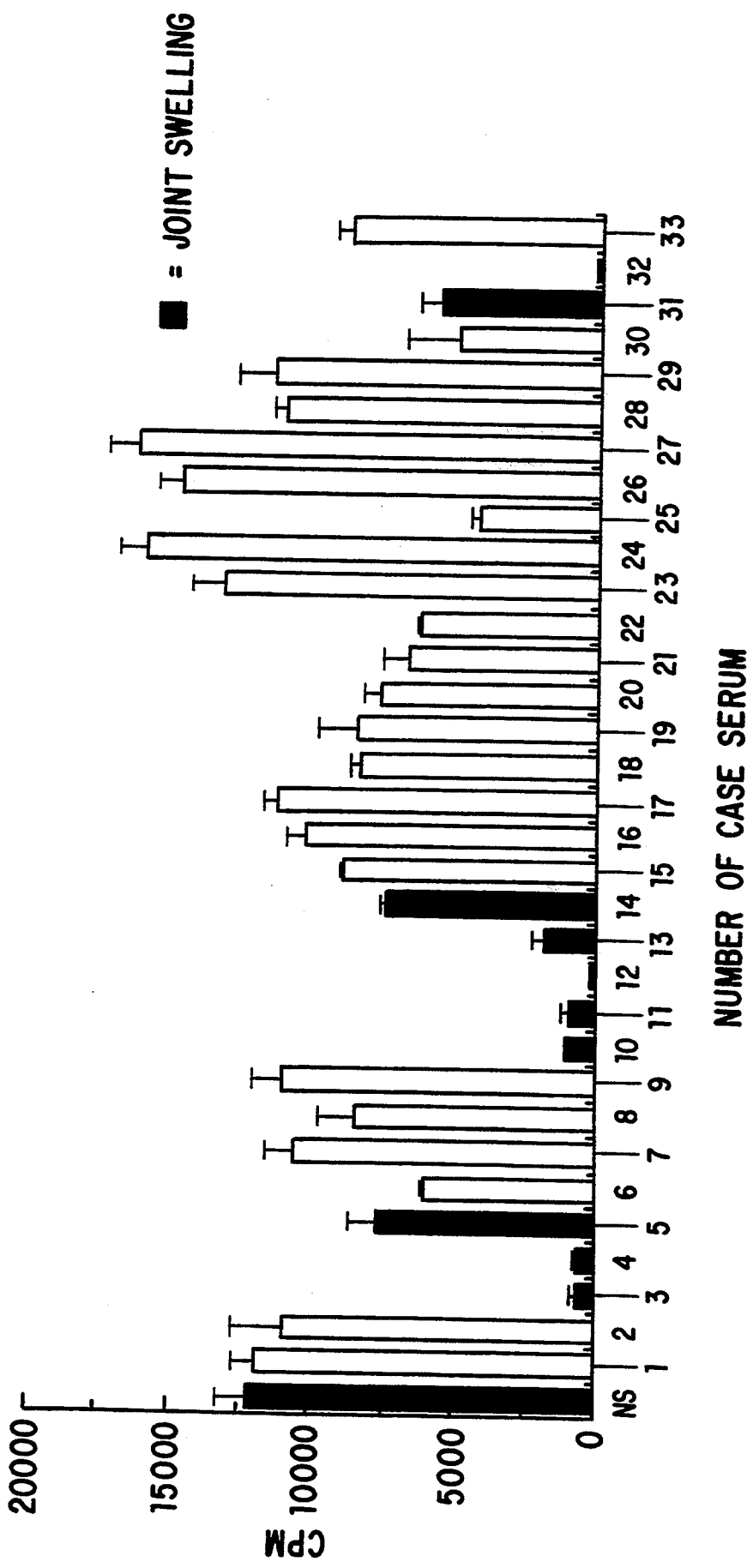

33 individual serum from patients diagnosed by a physician as having symptoms compatible with Lyme disease were analyzed as described in Example 12. FIG. 12 summarizes the borreliacidal activity. 24 of 33 Lyme disease patients killed at least 10% of the added B. burgdorferi compared to pooled normal serum. When the patients who did not meet the strictest Center for Disease Control definition of Lyme disease were omitted, 20 of 20 case-defined sera caused reductions from 7 to 100%. In addition, 10 of 10 (100%) patients with joint swellings killed 38 to 100% of the B. burgdorferi.

EXAMPLE 16

Figure 13:
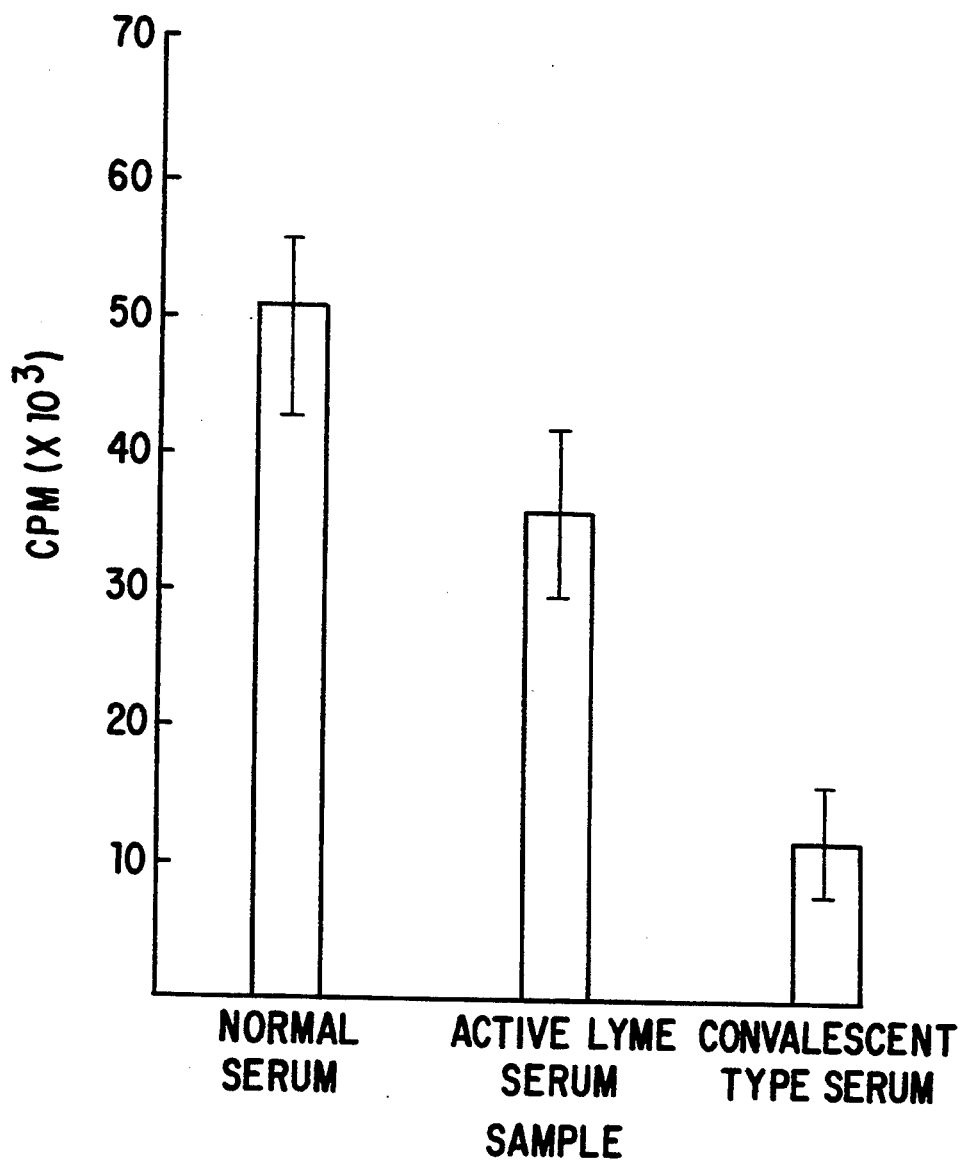

An acute and convalescent serum from a Lyme disease patient was analyzed as described in Example 12. FIG. 13 demonstrates that borreliacidal activity increased over time after infection with B. burgdorferi.

EXAMPLE 17

Figure 14:
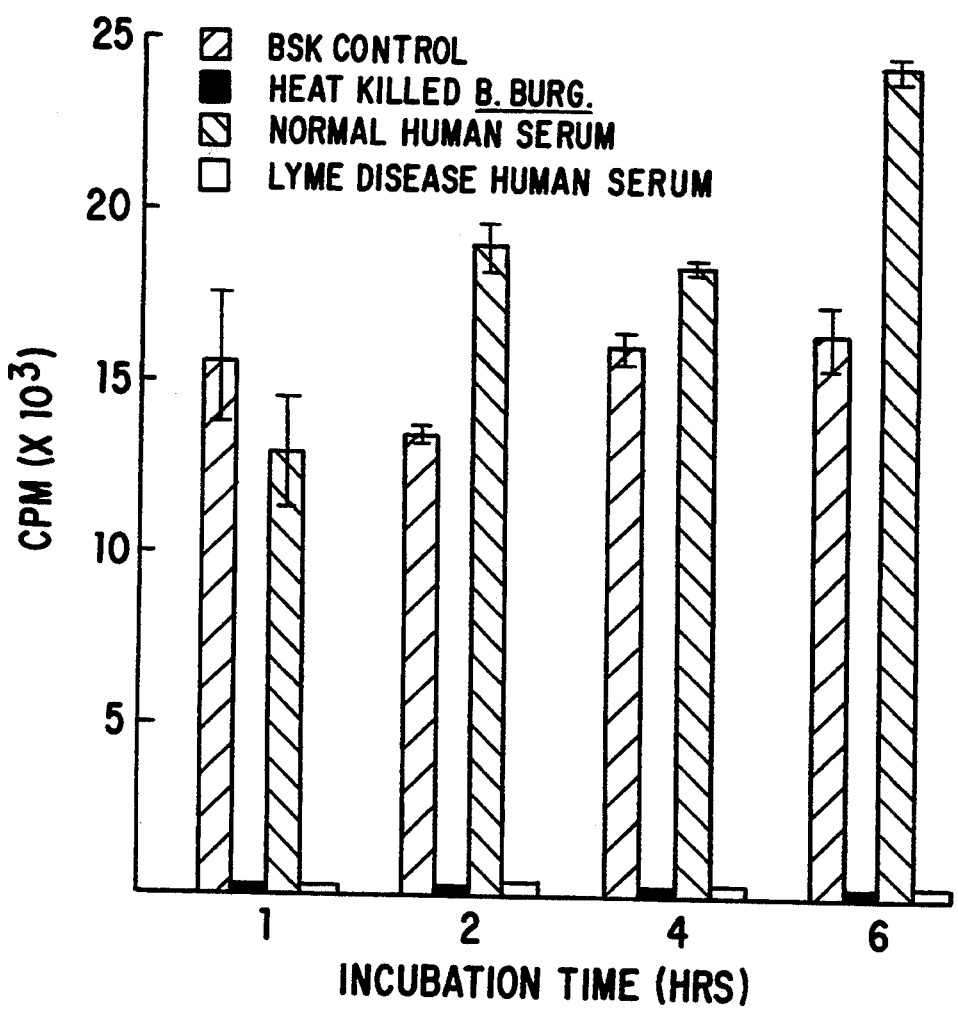

A Lyme disease serum and a normal human serum were assayed as described in Example 12 to determine how fast in vitro borreliacidal activity occurred. Identical samples were incubated for 1, 2, 4 or 6 hours at 32° C. before adding $^3$H-adenine and BSK. FIG. 14 demonstrates that borreliacidal activity occurred as early as 1 hour after exposure of B. burgdorferi to Lyme disease serum.

EXAMPLE 18

A counting assay which physically (mechanically) counts single bacteria was developed to increase the sensitivity and reproducibility of the assay and to eliminate the need for radioactive labels. The assay was performed essentially as stated in Example 1 and 12 except complement was added so that agglutination would not occur and individual organisms could be counted. After an initial incubation of 2 hours, 800 ul of fresh BSK was added and the assays were incubated for 1–4 days to allow remaining organisms to multiply. After this incubation, the number of B. burgdorferi in aliquots of the individual samples was determined using a Coulter counter equipped with a 30 micron aperture.

EXAMPLE 19

Figure 15:
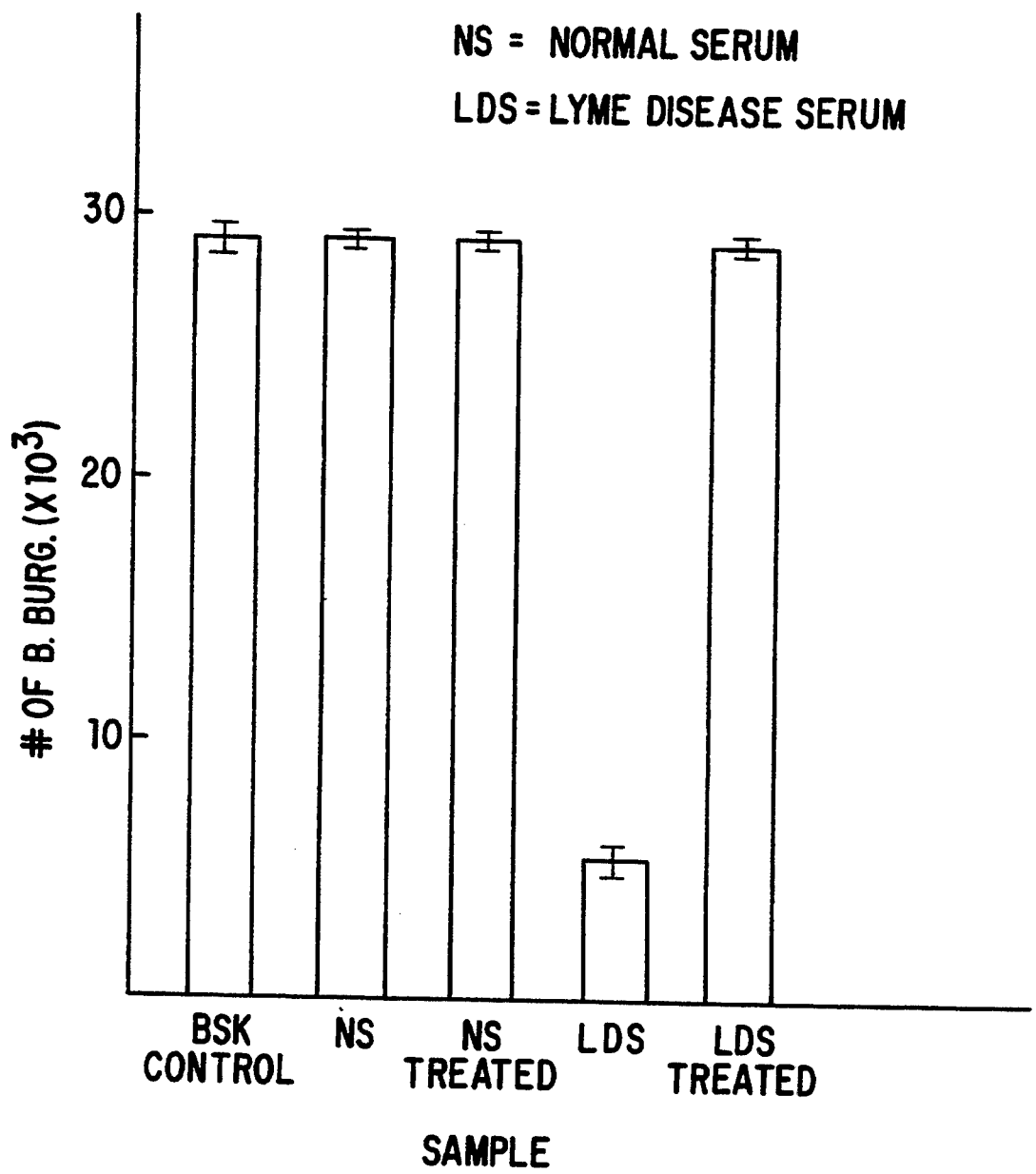

A normal serum and a Lyme disease serum were assayed for borreliacidal activity before and after treatment with human anti-IgG as described in Example 18. FIG. 15 demonstrates that treatment with anti-IgG did not affect normal serum. However, the removal of antibodies with anti-human IgG caused human Lyme disease serum to lose its borreliacidal activity. These results demonstrate that specific antibody is responsible for the borreliacidal activity in human Lyme disease serum.

EXAMPLE 20

We have found that we can use labeling of B. burgdorferi with propidium iodide (15 ug/ml for 30 minute incubation) and flow cytometry to detect killed B. burgdorferi within 2 hours after the Lyme spirochete is added to case-defined serum with complement. Flow cytometry is used to count individual labelled bacteria. This method can determine live and dead bacteria by distinguishing between labelled and unlabelled bacteria.

EXAMPLE 21

Figures 16, 17:
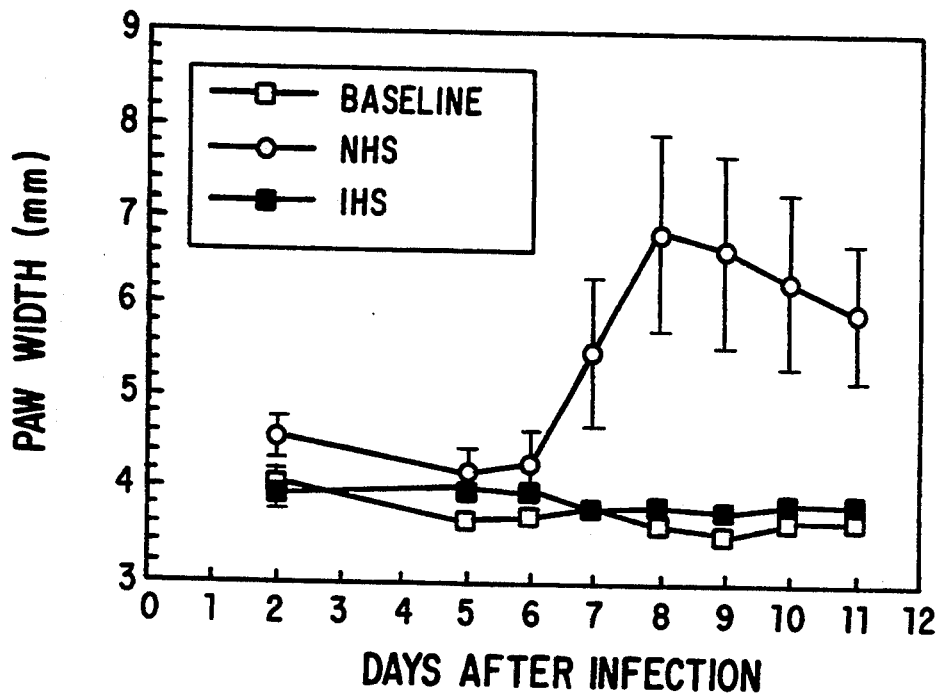

A case-defined Lyme disease serum was selected that demonstrated borreliacidal activity using our in vitro assay. The heat-inactivated serum was then injected intraperitoneally (0.5 ml) into 3 hamsters that were subsequently challenged with B. burgdorferi. Normal human serum (non-case) was included as a control. FIG. 16 demonstrates that the human Lyme disease serum (*B. burgdorferi* positive serum) provided passive immunity and prevented hamsters from developing Lyme arthritis. More importantly, the case-defined Lyme serum killed *B. burgdorferi* in the hamsters (FIG. 17). No spirochetes were recovered from the tissues of the hamsters. In contrast, spirochetes were recovered from the tissues of hamsters given normal (non-case) serum. These results also demonstrate that the in vitro assay of the present invention is a reliable predictor of immune status.

From the foregoing, it will be apparent to those skilled in the art that various modifications in the above-described methods, compositions, and articles of manufacture can be made without departing from the spirit and scope of the present invention. Accordingly, the present invention may be embodied in other specific forms without departing from the spirit or essential characteristics thereof. Present embodiments and examples, therefore, are to be considered in all respects as illustrative and not restrictive, the scope of the present invention being indicated by the appended claims rather than by the foregoing, and all changes which come within the meaning and range of equivalency of the claims are therefore intended to be embraced therein.

We claim:

1. A method of performing an assay to determine whether a patient has been exposed to *Borrelia burgdorferi*, said method comprising:
   collecting serum from a patient which may have been exposed to *Borrelia burgdorferi*;
   preparing a sample mixture, said sample mixture comprising a portion of said patient's serum and an inoculum of viable *Borrelia burgdorferi* organisms;
   incubating said sample mixture;
   determining the number of viable organisms remaining in said sample mixture after incubation; and
   comparing said number with the quantity of viable organisms remaining in a control mixture.

2. The method of claim 1 wherein said serum is heat inactivated before preparation of said sample mixture.

3. The method of claim 1 wherein said *Borrelia burgdorferi* organisms are of a strain selected from the group consisting of strain 297, strain B31 and a strain indigenous to the area in which said patient is suspected to have been exposed to *Borrelia burgdorferi*.

4. The method of claim 3 wherein said *Borrelia burgdorferi* organisms are of strain 297.

5. The method of claim 3 wherein said *Borrelia burgdorferi* organisms are of a strain indigenous to the area in which said patient is suspected to have been exposed to *Borrelia burgdorferi*.

6. The method of claim 1 wherein said *Borrelia burgdorferi* organisms are properly aged organisms.

7. The method of claim 1 wherein said sample mixture and said control mixture are incubated at 32° C.

8. The method of claim 7 wherein said sample mixture is incubated for at least about 30 minutes, 9. The method of claim 8 wherein said sample mixture is incubated for about 6 hours, 10. The method of claim 8 wherein said sample mixture is incubated for about.18 hours, 11. The method of claim 1 wherein said number of viable organisms remaining in said sample mixture and said quantity of viable organisms remaining in said control mixture are determined by counting viable *Borrelia burgdorferi* organisms under a microscope.

12. The method of claim 1 wherein said patient is human.

13. The method of claim 1 wherein said control mixture is prepared by mixing normal serum and an inoculum of viable *Borrelia burgdorferi* organisms, and wherein said control mixture is incubated with said sample mixture.

14. The method of claim 1 wherein said number of viable organisms remaining in said sample mixture and said quantity of viable organisms remaining in said control mixture are determined by measurement of uptake of $^3$H-adenine.

15. The method of claim 1 wherein said number of viable organisms remaining in said sample mixture and said quantity of viable organisms remaining in said control mixture are determined by flow cytometry or Coulter counter.

16. A method of performing an assay to determine whether a patient has been exposed to *Borrelia burgdorferi*, said method comprising:
   collecting serum from a patient which may have been exposed to *Borrelia burgdorferi*;
   heat inactivating said serum;
   preparing a sample mixture, said sample mixture comprising a portion of said patient's heat-inactivated serum and an inoculum of viable *Borrelia burgdorferi* organisms;
   incubating said sample mixture;
   determining the number of viable organisms remaining in said sample mixture after incubation; and
   comparing said number with the quantity of viable organisms remaining in a control mixture.

17. The method of claim 16 wherein said *Borrelia burgdorferi* organisms are of a strain selected from the group consisting of strain 297. strain B31 and a strain indigenous to the area in which said patient is suspected to have been exposed to *Borrelia burgdorferi*.

18. The method of claim 17 wherein said *Borrelia burgdorferi* organisms are of strain 297.

19. The method of claim 17 wherein said *Borrelia burgdorferi* organisms are of a strain indigenous to the area in which said patient is suspected to have been exposed to *Borrelia burgdorferi*.

20. The method of claim 16 wherein said *Borrelia burgdorferi* organisms are properly aged organisms.

21. The method of claim 16 wherein said sample mixture and said control mixture are incubated at 32° C.

22. The method of claim 21 wherein said sample mixture is incubated for at least about 30 minutes.

23. The method of claim 22 wherein said sample mixture is incubated for about 6 hours.

24. The method of claim 22 wherein said sample mixture is incubated for about 18 hours.

25. The method of claim 16 wherein said number of viable organisms remaining in said sample mixture and said quantity of viable organisms remaining in said control mixture are determined by counting viable *Borrelia burgdorferi* organisms in said sample mixture and in said control mixture using a microscope.

26. The method of claim 16 wherein said patient is human.

27. The method of claim 16 wherein said control mixture is prepared by mixing normal serum and an inoculum of viable *Borrelia burgdorferi* organisms, and wherein said control mixture is incubated with said sample mixture.

28. The method of claim 16 wherein said number of viable organisms remaining in said sample mixture and said quantity of viable organisms remaining in said control mixture are determined by measurement of uptake of $^3$H-adenine.

29. The method of claim 16 wherein said number of viable organisms remaining in said sample mixture and said quantity of viable organisms remaining in said control mixture are determined by flow cytometry or Coulter counter.

30. A method of performing an assay to determine whether a patient has been exposed to *Borrelia burgdorferi*, said method comprising:

collecting serum from a patient which may have been exposed to *Borrelia burgdorferi*;

preparing a sample mixture, said sample mixture comprising a portion of said patient's serum, an inoculum of viable *Borrelia burgdorferi* organisms, and added complement;

incubating said sample mixture;

determining the number of viable organisms remaining in said sample mixture after incubation; and comparing said number with the quantity of viable organisms remaining in a control mixture.

31. A method of performing an assay to determine whether a patient has been exposed to *Borrelia burgdorferi*, said method comprising:

collecting serum from a patient which may have been exposed to *Borrelia burgdorferi*;

heat inactivating said serum;

preparing a sample mixture, said sample mixture comprising a portion of said patient's heat-inactivated serum, an inoculum of viable *Borrelia burgdorferi* organisms, and added complement;

incubating said sample mixture;

determining the number of viable organisms remaining in said sample mixture after incubation; and comparing said number with the quantity of viable organisms remaining in a control mixture.

32. The method of claim 1 wherein said sample mixture further comprises added complement.

33. The method of claim 16 wherein said sample mixture further comprises added complement.

34. The method of claim 1 wherein said sample mixture further comprises BSK medium.

35. The method of claim 16 wherein said sample mixture further comprises BSK medium.

* * * * *